United States Patent [19]
Jones, Jr.

[11] Patent Number: 5,452,237
[45] Date of Patent: Sep. 19, 1995

[54] COINCIDENCE ERROR CORRECTION SYSTEM FOR PARTICLE COUNTERS

[75] Inventor: William R. Jones, Jr., Hialeah, Fla.

[73] Assignee: Abbott Laboratories, Abbott Park, Ill.

[21] Appl. No.: 203,217

[22] Filed: Feb. 28, 1994

[51] Int. Cl.$^6$ .............................................. G06F 17/00
[52] U.S. Cl. ..................................... 364/555; 73/865.5
[58] Field of Search .................... 364/555, 554, 571.02; 73/865.5

[56] References Cited

U.S. PATENT DOCUMENTS

| | | | |
|---|---|---|---|
| 3,557,352 | 1/1971 | Hogg et al. | 364/554 |
| 3,973,189 | 8/1976 | Angel et al. | 364/571.02 |
| 3,973,725 | 8/1976 | Watanabe et al. | 364/555 |
| 4,817,446 | 4/1989 | Kanamori | 364/555 |
| 5,247,461 | 9/1993 | Berg et al. | 364/554 |

OTHER PUBLICATIONS

Jameson; "Construction and Scanning, Photon-Counting Spectrofluorometer" Amer. Inst of Phy. 1976.

*Primary Examiner*—Ellis B. Ramirez
*Attorney, Agent, or Firm*—Richard D. Schmidt

[57] ABSTRACT

A multi-channel particle counting system corrects for coincidence errors by generating at least a first subtractive correction factor for any channel by taking counts from only channels that are lower than the particular channel being corrected. Optionally a second additive correction factor may be generated based on counts in all channels. The correction factor (s) are then, respectively subtracted from, or added to, the individual channel counts to generate an approximation of the true channel by channel counts.

13 Claims, 4 Drawing Sheets

COINCIDENCE ERROR CORRECTION SYSTEM FOR PARTICLE COUNTERS

A portion of the disclosure of this patent document contains material which is subject to a claim of copyright protection. The copyright owner has no objection to the facsimile reproduction by anyone of the patent document or the patent disclosure, as it appears in the Patent and Trademark Office file or records, but otherwise reserves all other rights whatsoever.

FIELD OF THE INVENTION

This invention relates to particle counters; more particularly, the invention relates to an improved method and apparatus for correcting, for so-called coincidence errors, the measured particle distribution of a particle population having various particle sizes.

BACKGROUND AND OBJECTS OF THE INVENTION

It is frequently desirable to determine the particle size distribution of a particle population having various particle sizes, such as may exist in blood. On the basis of the measured particle distribution, histograms are generated to form a basis for further medical analysis of the blood.

Particle counters, particularly those which generate an electrical signal the amplitude of which is proportional to the volume of particles passing through, or by, a counting zone, are subject to coincidence phenomena during which more than one particle will enter the counting zone almost simultaneously. In such cases, the particle counters will generate a signal proportional to the sum of the volume of the several particles and indicate the apparent presence of a single, larger particle, when in fact two (or more) smaller particles have passed through the counting zone. This creates an undesirable false count.

Typically also, prior art systems for generating particle size histograms have attempted to correct for errors in the observed, or raw counts, by applying correction factors of varying degrees of complexity and based on certain assumptions about the nature of the particle size distribution. Thus, for example, there have been suggested methods for coincidence correction based on an assumption that typical particle populations passing through counters will generate pulses forming a Poisson distribution. Other particle counters have attempted to modify raw counts generated by particle detectors in accordance with the time duration of the generated signals.

Yet other prior art systems vary the generated signal in accordance with the repetition rate of the generated particle signals.

Finally, coincidence error correction has been achieved by applying to the generated raw counts one or more fixed correction factors, based in part on characteristics of the particular particle counter.

Experimental verification of the effectiveness of various coincidence correction schemes has not been entirely successful.

Accordingly, it is a primary object of this invention to provide an improved coincidence error correction method and apparatus possessing improved experimental verifiability.

The occurrence of coincidence is an essentially random, statistical process. As a result, most coincidence error correction systems which employ statistical correction approaches are only approximations and depend on assumptions made about the theoretical particle distribution. This limits the accuracy of the generated data.

It is another object of this invention to provide a coincidence error correction regardless of the type of particle distribution being measured.

SUMMARY OF THE INVENTION

In accordance with the invention, coincidence error correction in a particle size counter is effected by generating from the channel by channel measured counts in a multi channel particle counter at least a first correction factor for each particular channel based on the statistical probability of coincidence of particles smaller than the size range for the particular channel count being corrected. This first correction factor is subtracted from the raw count for each channel to compensate for an over count as a result of the coincidence.

Because particle coincidence, when it occurs, results not only in a over count for any given channel, but also results in an under count of other sized channels, a second correction factor is calculated based on the raw count in all channels and is applied as an additive correction to the channel by channel raw count.

Both first and second correction factors are calculated for each channel and are based on probability functions using the accumulated channel by channel raw counts.

The corrected channel by channel count, whether using only one, or both, correction factors is then used to develop a histogram of the particle size distribution from which, in the case of blood analysis, certain other pertinent data is developed.

The foregoing and other objects, features and advantages of the invention will be apparent from the following more particular description of a preferred embodiment of the invention, as illustrated in the accompanying drawings.

DETAILED DESCRIPTION

Figure 1:
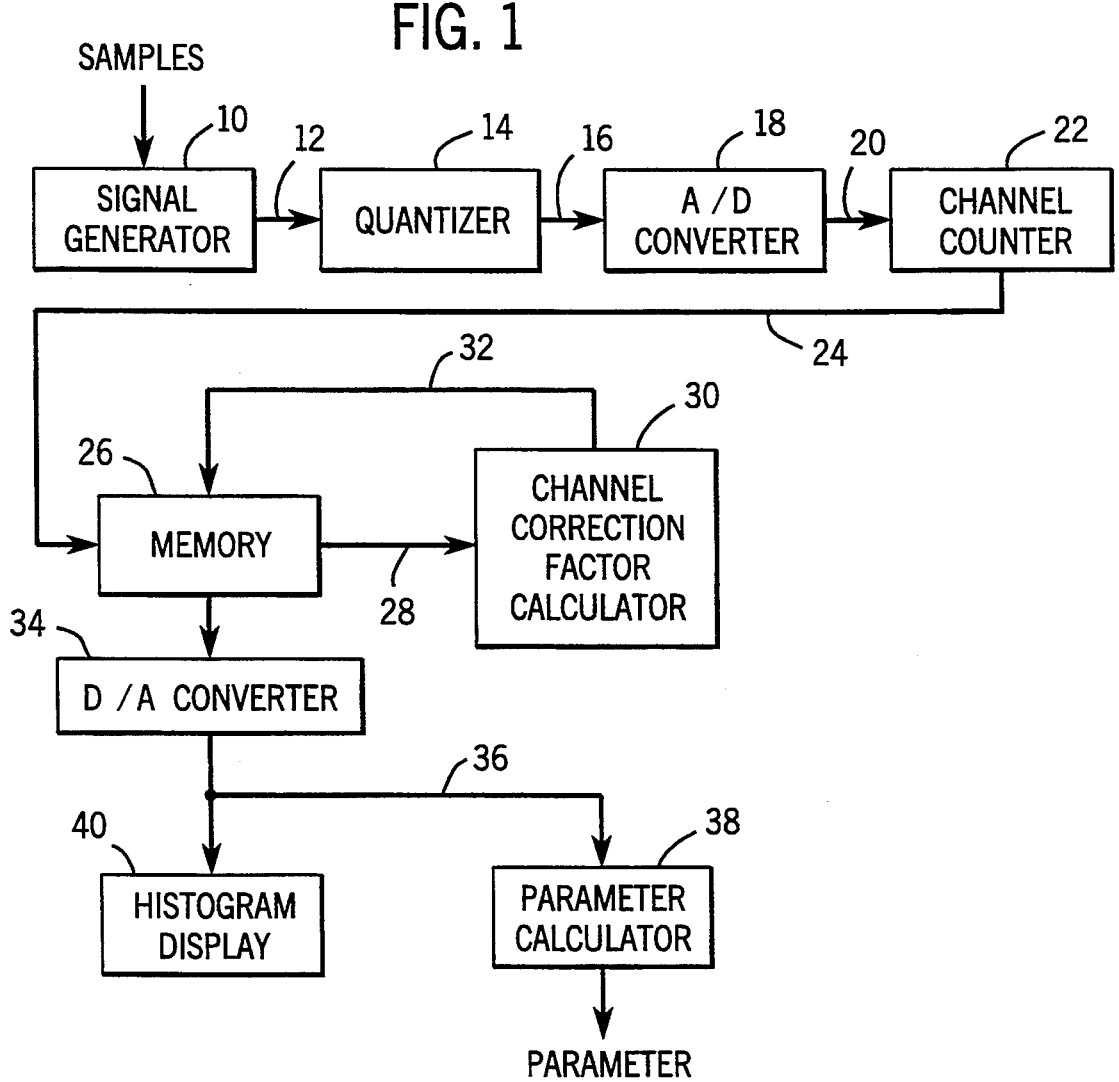
FIG. 1 is a functional block diagram of the components of a channel by channel coincidence error correction system.
Figure 2:
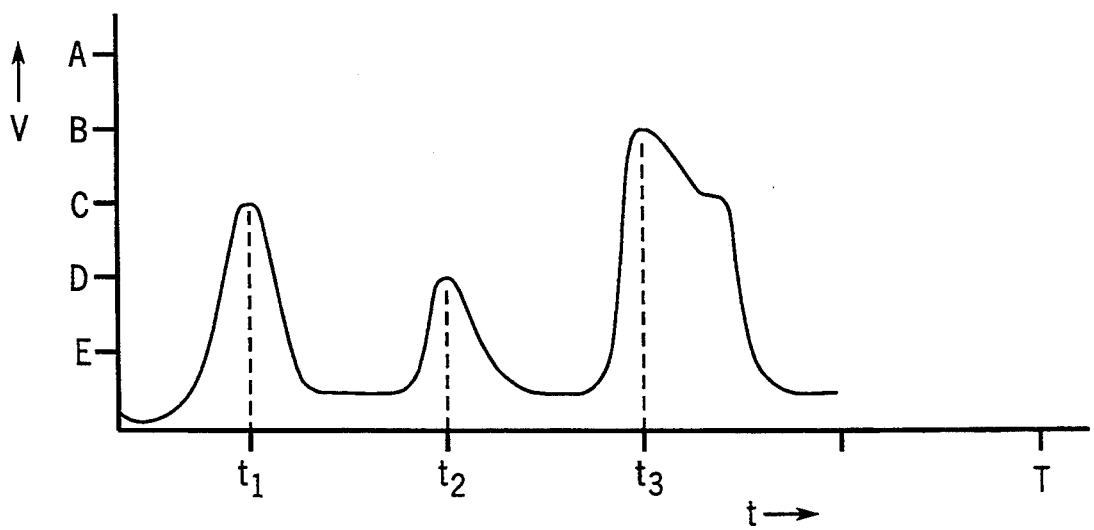
FIG. 2 is a diagram of a typical electrical signal waveform generated by a particle counter.

With reference to FIG. 1, a sample of a particle population of various particle sizes is passed through a signal generator 10 which generates a electrical signal proportional to the volume of the particle sizes passing through the signal generator 10 at any given time t1, t2, t3. The time varying signal from signal generator 10 is applied via a conduit 12 to a quantizer 14 which determines the amplitude of the time varying signal, such as shown in FIG. 2, at various quantization levels, A, B, C, D, and E at various time periods t1, t2, t3. The quantization levels represent channels and can be chosen at any number of levels. The resulting quantized signals are provided to an analog digital converter 18 via a conduit 16 so that the quantized analog signals can be converted to a digital form.

A channel counter 22 then determines for each of the quantization channels, for example A-E, the number of particles registered in each channel at the various times t1, t2, t3 within a given count period T.

The resulting channel by channel counts are then provided to a memory 26 where they are stored for further processing.

The raw channel by channel counts accumulated in memory 26 are provided via a conduit 28 to a channel correction factor calculator (CCFC) 30 which calculates at least a first, and optionally a second, channel by channel correction factor to be applied to memory 26 via a conduit 32 where the correction factor is used to correct the raw counts of each channel.

The corrected channel by channel counts are then provided, via a digital to analog converter 34, to a parameter calculator 38 and to a histogram display 40.

When the particle size distribution is to be performed on a sample of blood, the resulting corrected particle distribution may be utilized for the straight forward calculation of various blood parameters such as mean cell volume (MCV) and red cell distribution width (RDW) and the histogram display 40 is provided for those medical personnel who additionally wish to view the histogram itself.

Before proceeding with a description of how the functional block diagram of FIG. 1 operates, a brief background discussion is necessary to explain the underlying reasoning involved in analyzing coincidence phenomena in particle detectors.

Coincidence, i.e., the generally simultaneous traversal of more than one particle through a counting aperture, leads to a situation in which one particle will not finish generating its pulse before another closely following particle starts generating another pulse. The phenomenon, when it occurs, leads to "dead time" which is the time that the counting aperture is unable to detect a particle because the previous particle has not finished passing through. To calculate the probability that a particle of size $s_j$ will pass through a counting aperture at the same time as a particle of size $s_i$, some definitions are in order:

$t_{Di}$ is the total dead time due to particles in the $i^{th}$ size interval during the whole counting interval;

$t_{di}$ is the dead time for a single particle in the $i^{th}$ size interval;

$t_c$ is the count time;

$n_i$ is the number of particles in the $i^{th}$ size interval counted during $t_c$.

The total dead time for any one channel is given by the expression:

$$t_{D1} = n_1 t_{d1} \quad (1)$$

The fraction of time that particles of any given size will be in the aperture is given by the following expression:

$$P = t_d/t_c \quad (2)$$

The probability of finding two different size particles in the counter aperture is given by the expression:

$$P_{12} = P_1 P_2 = t_{D1} t_{D2}/t^2_c \quad (3)$$

Thus, any particle counting system that has multiple channels (i.e., multiple quantization levels) needs to take into account the probability of coincidence events in each channel and must correct the measured, or raw, counts of each channel by the probability that coincidence has occurred.

Two effects of particle coincidence have to be considered, namely that of an overcount as a result of coincidence and an undercount.

As to an overcount, the following example is illuminating; considering that any given channel designed to measure particles having a volume of, say, six units, a signal representing that volume unit could be a true count if no coincidence effects had taken place. However, a signal reading of six could also have been given by the possible coincidence of particles of a volume 5 with a volume 1, or a volume 4 with a volume 2, or a volume 3 with a volume 3, passing coincidentally through the counting aperture. These three latter possible phenomena, if they took place, would result in a overcount for that particular channel. Similarly, a signal indicating the presence of a particle size 7 volume units could be result from the presence of only a single particle with size 7 volume units, in which case it would be a true count; however, a signal representing the presence of 7 volume units could also have been created by the coincidence of a size 6 particle with a size 1 particle, or the coincidence of a size 5 particle with a size 2 particle, or the coincidence of a size 4 particle with a size 3 particle.

For any channel j in a multi-channel particle size counting system employing a desired plurality of channels, the overcount probabilities are collected, i.e., summed, and is given as a first correction factor by the following expression:

$$P_j = \sum_{i=1}^{i=j-1} \begin{cases} P_{i,j-i}(\text{meas.}) & \text{if } j - i \geq i \\ 0 & \text{if } j - i < i \end{cases} \quad (4)$$

It is to be noted that the summation of the overcount probabilities for any channel j extends only to the next lower adjacent channel, since particles larger than size j cannot "fit" into channel j, but must be in some higher sized channel, i.e., k or higher.

Thus, to correct for the overcount represented by equation (4), the measured probability (based on the measured, or raw, count for that particular channel) must be reduced by the probability of the overcount, i.e., by the first correction factor that is generated in accordance with equation (4).

In addition to creating an overcount, coincidence effects also create an undercount because any i-sized particle can traverse a counting aperture with a j-sized particle (where j is greater than i) and remove it from its proper i channel by coincidence effects.

For any given channel j, the probability of an undercount is then given by the collection, or summation, from one to N, (where N is the number of channels) of the probability of the undercount, and is given by the following expression:

$$P_j = \sum_{i=1}^{i=n} \{P_{i,j}(\text{meas.})\} \quad (5)$$

To summarize, coincidence effects will cause both over and under counts and the measured, or raw, counts indicated in any channel have to be modified by respectively adding to, or subtracting from, the measured count the respective correction factors. Thus, the actual count of a channel is approximated by the following expression:

$$P_j \approx P_j(\text{meas.}) +$$

$$\sum_{i=i}^{i=n} \left( P_{i,j}(\text{meas.}) - \sum_{i=1}^{i=j-1} \left\{ \begin{array}{l} P_{i,j}(\text{meas.}) \text{ if } j - i \geq i \\ 0 \text{ if } j - i < i \end{array} \right\} \right)$$

It is to be noted that the probability $P_{uv}$ is defined as equaling $n_u n_v t_{du} t_{dv}/t^2_c$.

For a typical particle counting system which may have as many as 256 channels, $t_d$ can have a typical range of 60 microseconds for the smallest particle channel decreasing monotonically to about 30 microseconds for the largest particle channel, while $t_c$ is on the order of 8 to 12 seconds.

Figure 3:
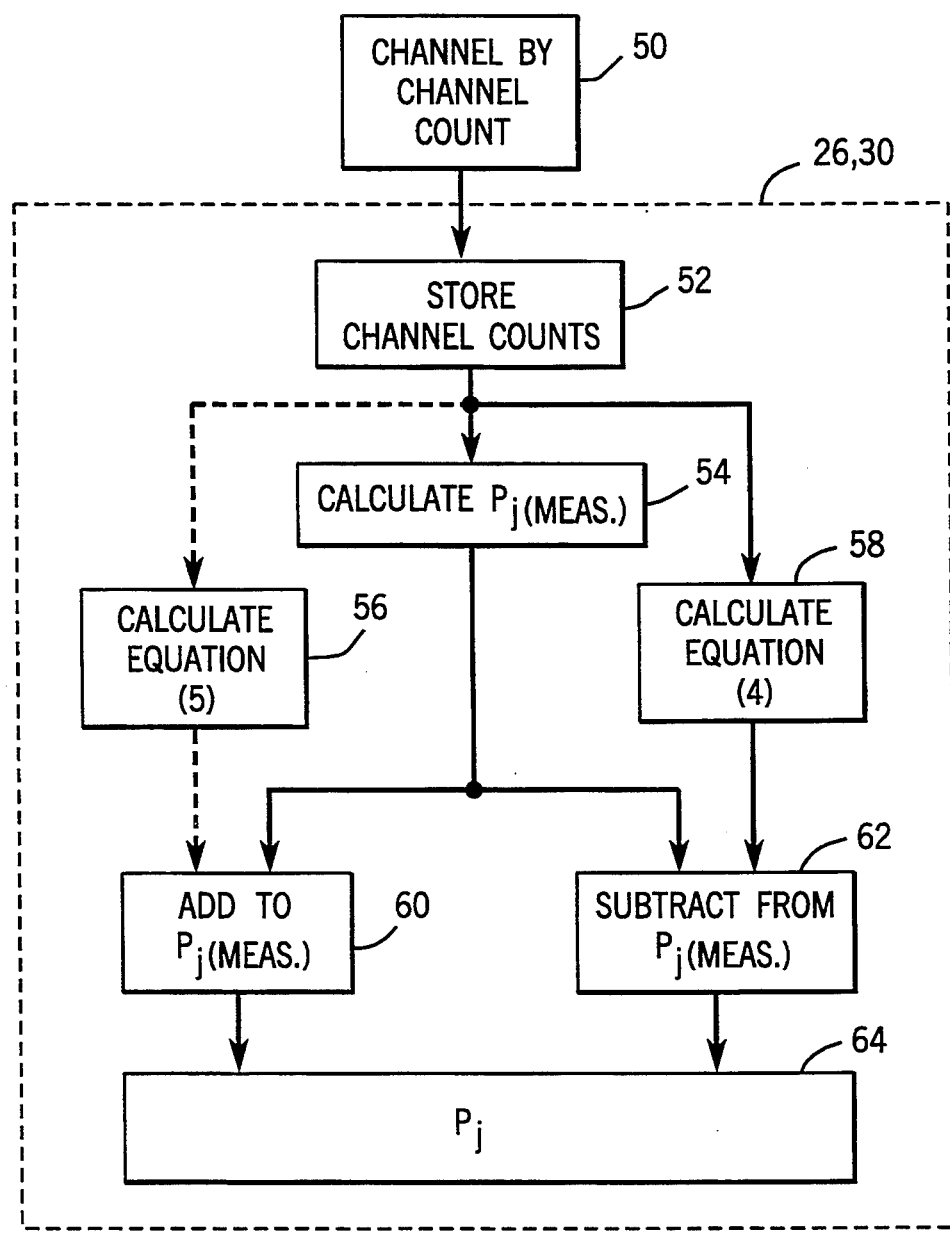
FIG. 3 is a flow chart of the functions performed by the coincidence error correction system of the invention.

With reference now to FIG. 3, there is described the sequence of functions performed by units 26 and 30 of the functional block diagram of FIG. 1. The channel by channel counts developed by the particle counting system in step 50 are stored in step 52 in the memory 26. Thereafter the CCFC unit 30 calculates $P_j$(measured) in step 54 and also calculates at least, in step 58, a first correction factor, given by equation (4), representing the overcount. Optionally., CCFC 30, also, in step 56, will calculate the expression given by equation (5), to calculate a second correction factor representing the undercount. Both correction factors are then respectively added to, or subtracted from, $P_{j(meas.)}$ in steps 60 and 62 to yield the probabilistic estimation of $P_j$ in step 64. All these steps can be achieved through a simple computer program, a listing for which, written in C code, is attached hereto as Exhibit "A".

Figure 4:
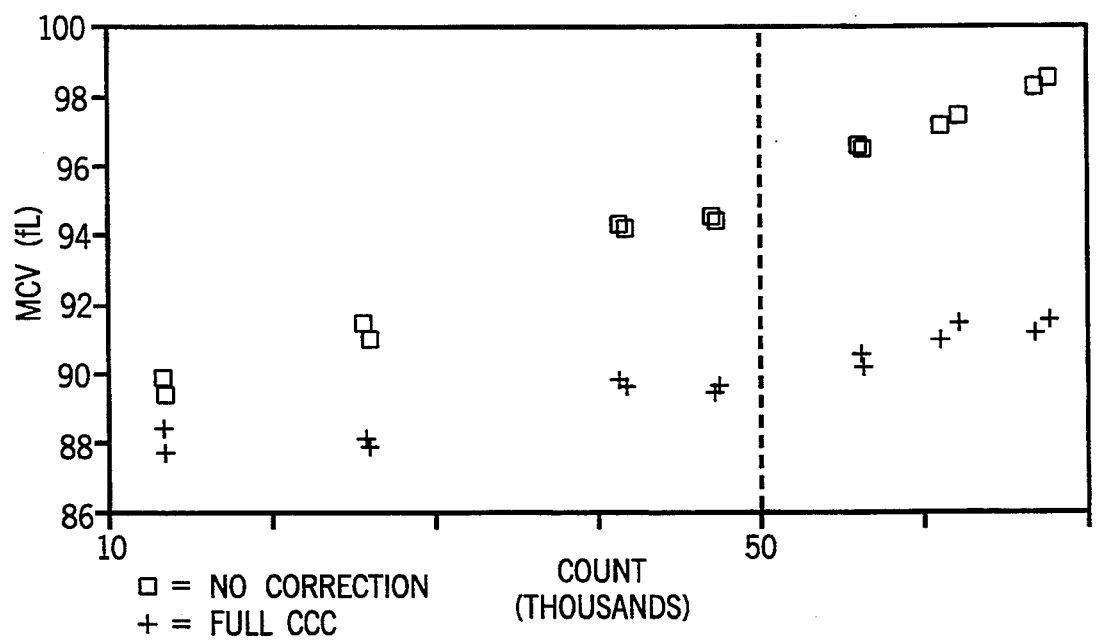
FIG. 4 is a graph of experimental data corrected for coincidence error by the use of two, a first, and a second, correction factors.
Figure 5:
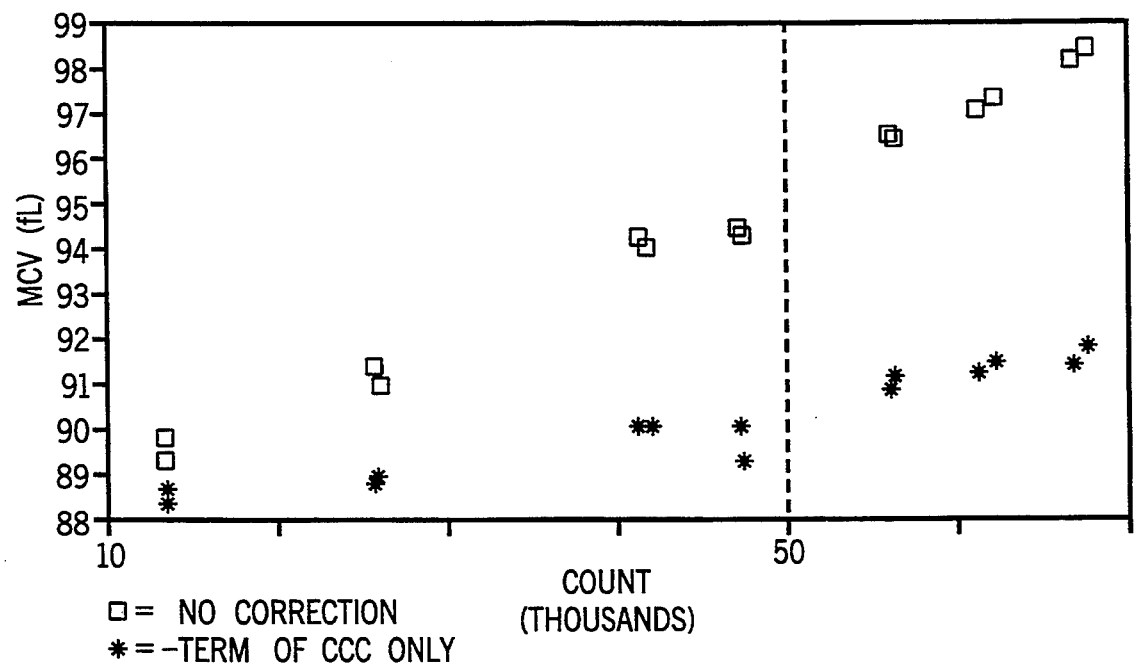
FIG. 5 shows experimental data corrected for coincidence errors utilizing only a first correction factor.
Figure 6:
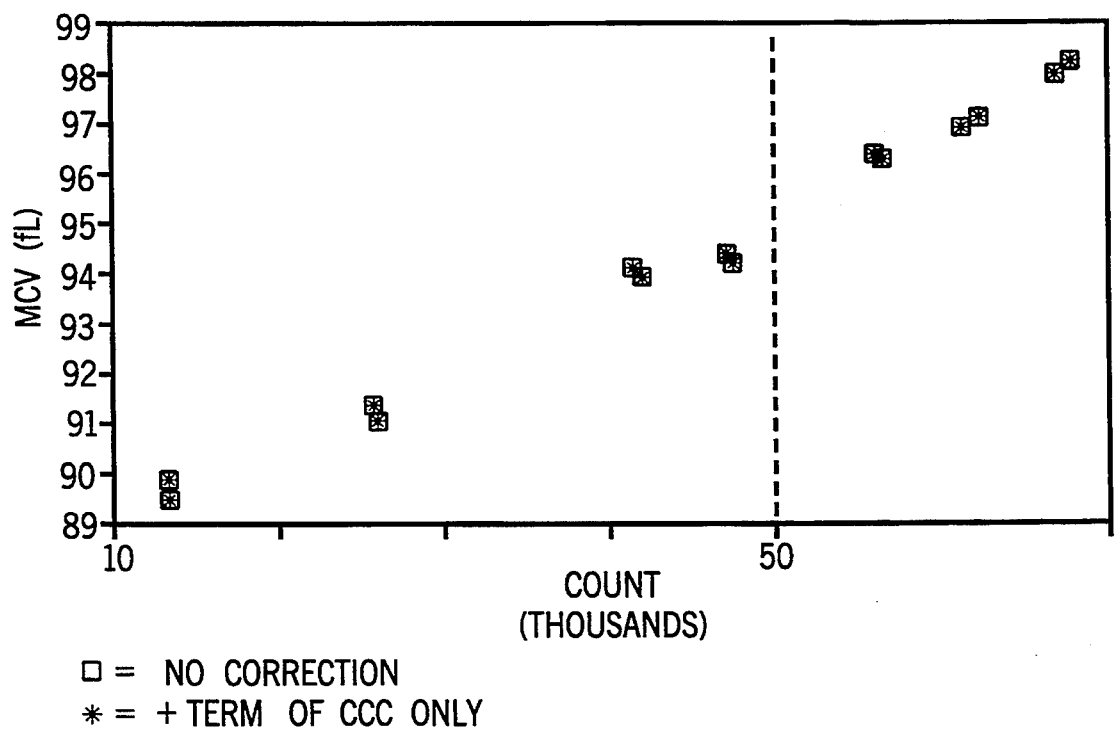
FIG. 6 shows experimental data corrected using only a second correction factor.

The efficacy of a particle counting system implemented according to the invention is illustrated in FIGS. 4, 5, and 6 where there is represented the calculated mean cell volume (MCV) of red blood cells in a blood sample. The vertical axis of each graph represents MCV in femtoliters, a unit of volume typically used in blood analysis, and the horizontal axis represents the particle count in thousands. As the graph in FIG. 4 illustrates, the MCV value of an uncorrected blood sample count shows MCV values rising as the particle count increases, when there is no physical reason for such an increase, while the correction, using both first and second correction factors according to the invention, yields a nearly straight line which is much more in accordance with physical reality.

To assess the respective efficacities of the first and second correction factors by themselves, the graphs of FIGS. 5 and 6 show that the first correction factor described above, namely to correct for overcounts, yields MCV values which are somewhat sloped (FIG. 5), but not nearly as much as the uncorrected values. The graph in FIG. 6 shows that use of only the second correction factor described above, to correct for undercounts, yields results which are difficult to distinguish from the uncorrected values. It thus appears that of the two correction factors described above, the first one, the one to correct for overcounts, appears to be the single more important one of the two described. It is thus entirely possible to implement the invention with use of only the first correction factor.

While the invention has been particularly shown and described with reference to preferred embodiment thereof, it will be understood by those skilled in the art that the foregoing and other changes in form and details may be made therein without departing from the spirit and the scope of the invention.

What is claimed is:

1. Apparatus for counting particles in a particle population of various particle sizes with correction for particle coincidence in the counting apparatus, comprising:
    (a) a signal generator for generating a signal proportional to the volume of particles sensed by the signal generator;
    (b) quantizer means responsive to the signal for producing a first plurality of signals, each one of said first plurality of signals representing a particular particle size range in the particle population, each particle size range defining a channel;
    (c) analog to digital conversion means responsive to the first plurality of signals for producing a second plurality of signals in digital form, each one of said second plurality of signals representing a particular particle size range in the particle population;
    (d) counting means responsive to the second plurality of signals for producing a particle count in each size range of the particle population;
    (e) a memory for storing the particle count produced in each particle size range;
    (f) channel by channel coincidence correction factor calculating means responsive to the particle count in each channel stored in the memory including means for calculating from the measured particle count in a particular channel a probability of the measured count and for also calculating from the particle count of each channel lower than the particular channel an overcount probability factor to be subtracted from the probability of the measured count, for that particular channel, and
    (g) means for subtracting from the probability of the measured count in a particular channel the overcount probability factor of each channel lower than the particular channel to generate the probability of an actual count for that particular channel.

2. Apparatus according to claim 1 wherein the channel by channel coincidence correction factor calculating means further includes means for calculating from the particle count of all channels an undercount probability factor to be added to the probability of the measured count for that particular channel.

3. Apparatus according to claim 1 wherein the overcount probability factor for a particular channel j is defined by the expression:

$$P_j = \sum_{i=1}^{i=j-1} \left\{ \begin{array}{l} P_{i,j-i}(\text{meas.}) \text{ if } j - i \geq i \\ 0 \text{ if } j - i < i \end{array} \right.$$

where $$P_{i,j-i}(\text{meas.}) = n_i n - i t_i t_{j-i}/t^2_c$$

$n_i$ is the raw particle count measured for any channel i counted during $t_c$;

$n_j$ is the raw particle count measured for any channel j counted during $t_c$;

$t_i$ is the assigned dead time for a single particle in channel i;

$t_j$ is the assigned dead time for a single particle in channel j;, and $t_c$ is the total amount time for all channels, and dead time is the time the signal generator is unable to detect a particle because of coincidence.

4. Apparatus according to claim 2 wherein the undercount probability factor for a particular channel is defined by the expression:

$$\sum_{i=1}^{i=n} \{P_{i,j}(\text{meas.})\}$$

where $$P_{i,j}(\text{meas.}) = n_i n_j - i t_i t_j / t^2_c$$

$n_i$ is the raw particle count measured for any channel i converted during $t_c$;

$n_j$ is the raw particle count measured for any channel j counted during $t_c$;

$t_i$ is the assigned dead time for a size particle in channel i;

$t_j$ is the assigned dead time for a size particle in channel j;

$t_c$ is the total amount time for all channels, and dead time is the time the signal generator is unable to detect a particle because of coincidence, and N is the total number of channels in the particle counting system.

5. Method for correcting the measured counts in a multiple channel particle counting system for particle coincidences which may occur in each channel, comprising:

(a) a generating a measured count for each channel;

(b) storing the measured counts for each channel generated in step (a) in a memory;

(c) calculating from each measured count stored in step (b) a probability of the measured count for each channel;

(d) calculating from the measured counts stored in step (b) an overcount probability correction factor for a particular channel which is based on the probability of overcounts in each channel lower than the particular channel, and (e) subtracting the overcount probability correction factor calculated in step (d) from the probability of the measured count probability calculated in step (b) for each one of the multiple channels.

6. A method according to claim 5 further including the additional steps of:

(f) calculating from the measured counts stored in step (b) an undercount probability correction factor for a particular channel which is based on the probability of undercounts in all the channels, and (g) adding the undercount probability correction factor calculated in step (b) to the measured count probability calculated in step (c) for each one of the multiple channels.

7. Method according to claim 5 further including the step of storing the results of step (e) in a memory.

8. Method according to claim 6 further including the step of storing the results of step (g) in a memory.

9. Method according to claim 5 wherein step (c) further comprises the step of storing the results of step (c) in a memory.

10. Method according to claim 5 wherein step (c) is performed in accordance with the equation:

where $$P_j = n_j t_{dj}/t_c$$

$n_j$ is the measured count in a particular channel j;

$t_{dj}$ is the assigned value for the dead time for one particle size j, and $t_c$ is the count period.

11. Method according to claim 5 wherein step (d) further comprises the step of storing the results of step (d) in a memory.

12. Method according to claim 5 Wherein step (d) is performed in accordance with the statement:

$$\sum_{i=1}^{i=j-1} \begin{cases} P_{i,j-i}(\text{meas.}) & \text{if } j-i \geq i \\ 0 & \text{if } j-i < i \end{cases}$$

where $$P_{i,j-i}(\text{meas.}) = n_i n_{j-i} t_i t_{j-i}/t^2_c$$

$n_i$ is the raw particle count measured for any channel i counted during $t_c$;

$n_j$ is the raw particle count measured for any channel j counted during $t_c$;

$t_i$ is the assigned dead time for a single particle in channel i;

$t_j$ is the assigned dead time for a single particle in channel j;

$t_c$ is the total amount time for all channels, and dead time is the time the signal generator is unable to detect a particle because of coincidence.

13. Method according to claim 6 wherein step (f) is performed in accordance with the statement:

$$\sum_{i=1}^{i=n} \{P_{i,j}(\text{meas.})\}$$

where $$P_{i,j-i}(\text{meas.}) = n_i n_j t_i t_j/t^2_c$$

$n_i$ is the raw particle count measured for any channel i converted during $t_c$;

$n_j$ is the raw particle count measured for any channel j counted during $t_c$;

$t_i$ is the assigned dead time for a size particle in channel i;

$t_j$ is the assigned dead time for a size particle in channel j;

$t_c$ is the total amount time for all channels, and dead time is the time the signal generator is unable to detect a particle because of coincidence, and N is the total number of channels in the particle counting system.

* * * * *